US005972721A

United States Patent [19]

Bruno et al.

[11] Patent Number: 5,972,721

[45] Date of Patent: Oct. 26, 1999

[54] IMMUNOMAGNETIC ASSAY SYSTEM FOR CLINICAL DIAGNOSIS AND OTHER PURPOSES

[75] Inventors: John G. Bruno, Panama City, Fla.; Johnathan L. Kiel, Universal City; John P. Kilian, San Antonio, both of Tex.

[73] Assignee: The United States of America as represented by the Secretary of the Air Force, Washington, D.C.

[21] Appl. No.: 08/816,429

[22] Filed: Mar. 14, 1997

Related U.S. Application Data

[60] Provisional application No. 60/013,393, Mar. 14, 1996, abandoned.

[51] Int. Cl.[6] ........................... G01N 33/533; B03C 1/00

[52] U.S. Cl. ........................... 436/526; 436/534; 436/63; 436/824; 435/7.2; 435/7.24; 435/7.32; 209/213; 209/214; 209/232; 210/695; 210/222

[58] Field of Search .................................. 209/2, 3, 214, 209/232; 210/222, 695; 422/57, 58, 59, 61, 68.1; 435/7.2, 7.21, 7.24, 7.32; 436/526, 534, 63, 824

[56] References Cited

U.S. PATENT DOCUMENTS

| | | | |
|---|---|---|---|
| 5,439,586 | 8/1995 | Richards et al. | 210/222 |
| 5,514,340 | 5/1996 | Lansdorp et al. | 422/101 |
| 5,602,042 | 2/1997 | Farber | 436/526 |

OTHER PUBLICATIONS

J.P. Hancock et al., A Rapid and Highly Selective Approach to Cell Separations Using an Immunomagnetic Colloid, Journal of Immunological Methods, vol. 164, pp. 51–60, 1993.

P.A. Liberti et al., Analytical–and Process–Scale Cell Separation with Bioreceptor Ferrofluids and High–Gradient Magnetic Separation, Cell Separation Science and Technology (Kompala and Todd, Eds.), American Chemical Society, Washington, D.C., Chap. 17, pp. 268–288, 1991.

S. Miltenyi et al., High Gradient Magnetic Cell Separation with Macs, Cytometry, vol. 11, pp. 231–238, 1990.

J.G. Treleaven et al., Removal of Neuroblastoma Cells From Bone Marrow with Monoclonal Antibodies Conjugated to Magnetic Microspheres, The Lancet, pp. 70–73, Jan. 14, 1984.

*Primary Examiner*—Carol A. Spiegel
*Attorney, Agent, or Firm*—Fredric L. Sinder; Thomas L. Kundert

[57] ABSTRACT

An apparatus and method for immunomagnetic separation and concentration of target biological materials is disclosed. The immunomagnetic separation is performed by a magnetic flow cell, or filter block, as part of an automated mostly continuous immunomagnetic assay system. The magnetic flow cell has two bundles of ferromagnetic rods or pins positioned inside an internal chamber so that a fluid sample flowing through the flow cell passes through the pins. A pair of cobalt magnets flank the flow cell so that the pins concentrate and sufficiently increase the magnetic fields so that even nanometer size magnetic beads can be captured. The overall system combines a reaction subsystem for reacting coated magnetic beads with a sample, a collection subsystem for capturing magnetic beads, a rinsing subsystem for removing debris and a filtering subsystem for removing captured magnetic beads from the collection subsystem. The new magnetic flow filter is the key component for the collection and filtering subsystems.

10 Claims, 3 Drawing Sheets

IMMUNOMAGNETIC ASSAY SYSTEM FOR CLINICAL DIAGNOSIS AND OTHER PURPOSES

CROSS-REFERENCE TO RELATED APPLICATIONS

This application claims priority under 35 U.S.C. § 119(e) from U.S. Provisional Application No. 60/013,393, filed Mar. 14, 1996, now abandoned, by applicants John G. Bruno, Johnathan L. Kiel and John P. Kilian, entitled Immunomagnetic Assay System for Clinical Diagnosis and Other Purposes. The invention description contained in that provisional application is incorporated by reference into this description.

RIGHTS OF THE GOVERNMENT

The invention described herein may be manufactured and used by or for the Government of the United States for all governmental purposes without the payment of any royalty.

BACKGROUND OF THE INVENTION

The present invention relates generally to apparatus and methods for immunomagnetic separation and concentration of target biological materials, and more specifically to an automated flow-through immunomagnetic assay system that rapidly and efficiently captures all types of immunomagnetic beads from fluid samples.

Immunomagnetic separation and concentration of specific target ligands or particles, such as bacteria or leukocytes, from complex mixtures, such as bone marrow, blood and other body fluids, is an increasingly popular technique for identifying biological pathogens. In this technique, antibodies to the bacteria or other pathogen of interest are immobilized on magnetic beads. The beads, with the attached antibodies, are mixed with the media being investigated so that molecules of any target organisms present in the media attach to the antibodies, and thus to the magnetic beads. The beads are then separated from the mix by a magnetic field and the now more concentrated mix of captured target organisms (if the target organisms were present in the original mix) tested by a variety of detection methods, such as ELISA, flow cytometry, automated microscopy and electrochemiluminescence (ECL) assay, for the presence of the target organism. To the extent that immunomagnetic assay systems can be made more effective and more rapid, they can be used for rapid clinical diagnosis of pathogens, toxins and other analytes in body fluids, rapid environmental detection of harmful bacteria, viruses and other substances in water and in industrial monitoring system for detection of harmful materials in foods and other substances.

A key element of any immunomagnetic assay system is a system for capturing the magnetic beads. Magnetic beads are, or typically contain, paramagnetic (that is, magnetizable in the presence of an external magnetic field, but nonmagnetic on removal of the field) magnetite ($Fe_3O_4$). Magnetic beads may range in diameter from 50 nm (colloidal "ferrofluids") to several microns. Ferrofluids are so small that they require magnetic fields greater than 4 Tesla per cm to capture them.

The prior art has shown that such relatively large field strengths may be generated by a small diameter wire that creates a high field gradient when placed in an external magnetic field. The small diameter wire acts as an antenna to concentrate the magnetic fields near it. The prior art has utilized this property in a number of existing immunomagnetic separation and detection methods and apparatus. One method has been to place steel wool inside a collecting vessel and then place the vessel inside a strong magnetic field. Another method has been to place paperclip-shaped bent metal pins inside microtitre wells and then move the holder for the microtitre wells inside a strong magnetic field. In the presence of the enhanced magnetic gradients, magnetic beads can be captured from any fluid samples inside the vessel or microtitre wells onto the steel wool or the bent metal pins. After the magnetic fields are removed, the captured magnetic beads can be removed from the steel wool or bent pins by various techniques. A third method described in the prior art for concentrating magnetic fields is a quadrupole magnetic arrangement which concentrates a magnetic field near the intersection of two north and two south poles of four bar magnets brought in close proximity.

The bent metal pins inside microtitre wells technique is primarily a batch process suitable for laboratory use. This technique can only process small batches of samples at one time.

The steel wool technique suffers from a number of disadvantages, a primary example of which is that steel wool-based systems are very difficult to clean completely and generally exhibit unacceptable levels of hysteresis, the tendency for later tests to show false results from contamination by leftover captured magnetic beads from previous tests.

In a quadrupole magnetic arrangement, the magnetic field strength is zero at the center of the arrangement, which requires designing a chamber to either eliminate cells in that area or depend on the magnetic beads sufficiently mixing to somewhat alleviate the problem.

Existing prior art techniques are not designed to accommodate all types of magnetic beads or are not fully automated. In particular, while suitable for laboratory work on small batches, they are not easily adaptable for continuous (or virtually continuous) monitoring for pathogens.

Thus it is seen that there is a need for an immunomagnetic assay system that can rapidly and efficiently capture all types of magnetic beads from milliliter quantities of fluid samples, and which can be used as part of a continuous process. The ability to run an immunomagnetic assay system on a continuous, or nearly continuous, basis is needed for immunomagnetic systems to find use in industry.

It is, therefore, a principal object of the present invention to provide an immunomagnetic assay system utilizing a flow cell for capturing magnetic beads that can rapidly and efficiently capture all types of magnetic beads from milliliter quantities of fluid samples.

It is a feature of the present invention that it works very rapidly.

It is another feature of the present invention that it will work will all sizes of magnetic beads.

It is an advantage of the present invention that it can be easily automated to provide a nearly continuous immunomagnetic assay system.

These and other objects, features and advantages of the present invention will become apparent as the description of certain representative embodiments proceeds.

SUMMARY OF THE INVENTION

The present invention provides an apparatus and method for immunomagnetic separation and concentration of target biological materials. A unique discovery of the present invention is a novel magnetic flow cell that rapidly and efficiently captures all types of immunomagnetic beads from fluid samples as part of an automated flow-through system. The inside of the new flow cell is shaped such that its volume expands where the fluid sample enters the flow cell to temporarily retard the flow of the fluid sample around a plurality of ferromagnetic rods and dramatically increase the number of captured magnetic beads.

Accordingly, the present invention is directed to a magnetic flow cell for capturing magnetic beads from a fluid sample as part of an immunomagnetic assay system, comprising a housing, a chamber inside the housing, an inlet port through the housing into the chamber for flowing a fluid sample into the chamber, an outlet port through the housing out from the chamber for flowing a fluid sample out of the chamber, a plurality of paramagnetic rods positioned inside the chamber such that a flowing liquid sample will flow past the paramagnetic rods as it flows through the chamber, and wherein the chamber is shaped so that its cross-sectional area expands from where it connects to the inlet port to a position past at least a plurality of the paramagnetic rods. The paramagnetic rods may also be positioned perpendicularly to an axis drawn between the inlet port and the outlet port.

The present invention is also directed to a magnetic flow cell for capturing magnetic beads from a fluid sample as part of an immunomagnetic assay system where the chamber may have any shape and the paramagnetic rods are positioned perpendicularly to an axis drawn between the inlet port and the outlet port.

The present invention is further directed to an automated immunomagnetic assay system, comprising a reaction subsystem for reacting coated magnetic beads with a sample in a solution to make a fluid sample, a collection subsystem for capturing magnetic beads out of the fluid sample, a rinsing subsystem for removing non-magnetic bead debris from the collection subsystem, and a filtering subsystem for removing captured magnetic beads from the collection subsystem and holding them for analysis. The collection and filtering subsystems may include a magnetic flow cell according to the present invention combined with a pair of movable magnets positioned such that they can move to and from a position flanking the magnetic flow cell.

The present invention is further directed to a method for capturing magnetic beads from a fluid sample as part of an immunomagnetic assay system, comprising the steps of flowing the fluid sample through a chamber, wherein the chamber includes a plurality of paramagnetic rods positioned inside the chamber such that the flowing liquid sample will flow past the paramagnetic rods as it flows through the chamber and wherein the chamber is shaped so that its cross-sectional area expands from where the fluid sample enters the chamber to a position past at least a plurality of the paramagnetic rods, and flanking the chamber with a pair of magnets as the fluid sample flows through the chamber. The paramagnetic rods may be positioned perpendicularly to the flow of fluid sample through the chamber.

The present invention is still further directed to a method for capturing magnetic beads from a fluid sample as part of an immunomagnetic assay system where the chamber may have any shape and the paramagnetic rods are positioned perpendicularly to the flow of fluid sample through the chamber.

The present invention is yet further directed to a method for performing an immunomagnetic assay on a sample, comprising the steps of reacting coated magnetic beads with the sample in solution to make a fluid sample, capturing the magnetic beads out of the fluid sample by the steps of flowing the fluid sample through a chamber, wherein the chamber includes a plurality of paramagnetic rods positioned inside the chamber such that the flowing liquid sample will flow past the paramagnetic rods as it flows through the chamber and wherein the chamber is shaped so that its cross-sectional area expands from where the fluid sample enters the chamber to a position past at least a plurality of the paramagnetic rods, and flanking the chamber with a pair of magnets as the fluid sample flows through the chamber, rinsing non-magnetic bead debris from the collection subsystem, and removing captured magnetic beads from the chamber by moving the pair of magnets away from a position flanking the chamber and flowing a buffer solution through the chamber. The paramagnetic rods may be positioned perpendicularly to the flow of fluid sample through the chamber.

The present invention is still further directed to a method for performing an immunomagnetic assay on a sample where the chamber may have any shape and the paramagnetic rods are positioned perpendicularly to the flow of fluid sample through the chamber.

DESCRIPTION OF THE DRAWINGS

The present invention will be more clearly understood from a reading of the following detailed description in conjunction with the accompanying drawings wherein.

DETAILED DESCRIPTION

Figure 1:
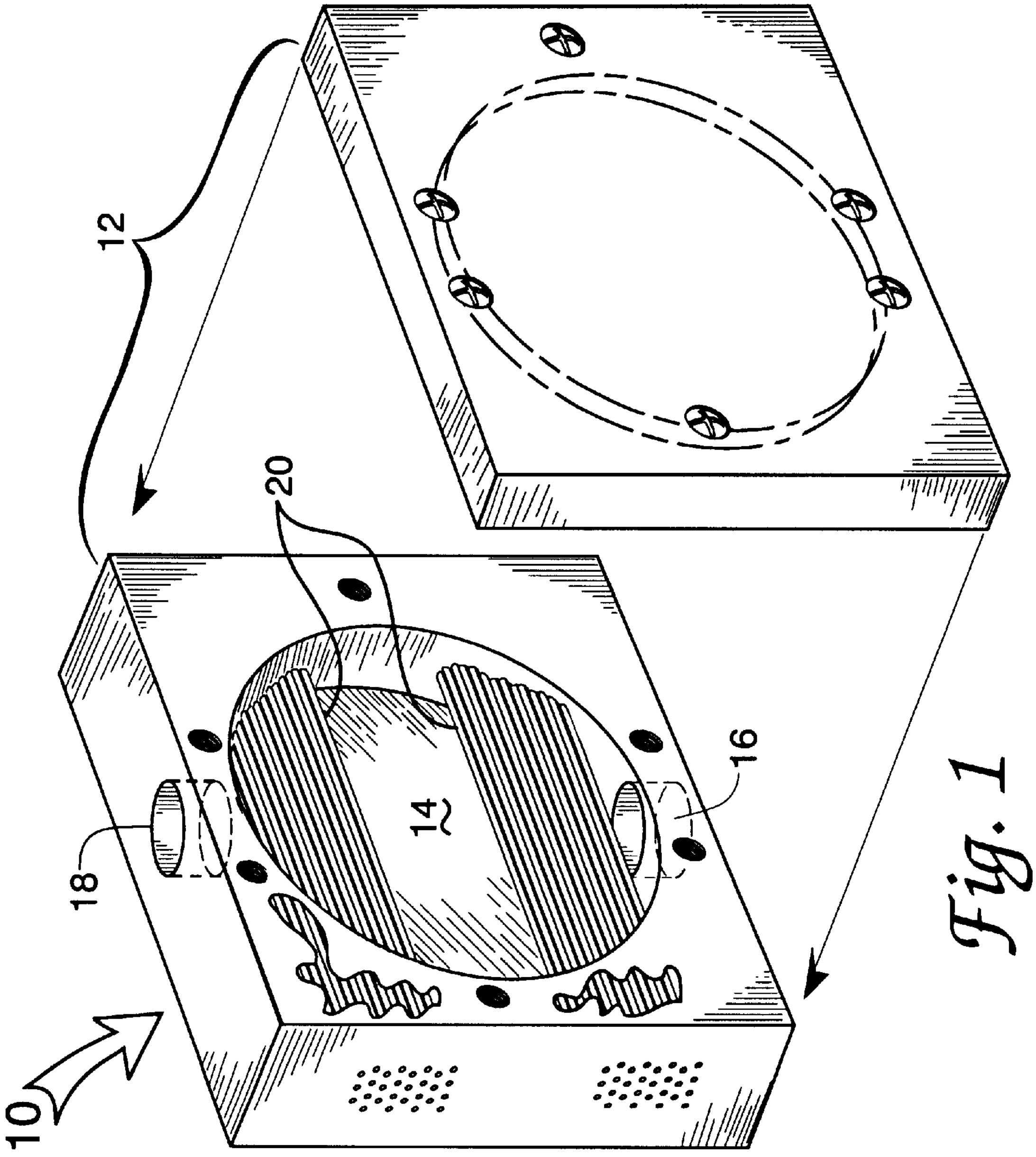
FIG. 1 is a perspective phantom view of a magnetic flow cell made according to the teachings of the present invention showing its interior cavity and bundles of ferromagnetic rods.
Figure 3:
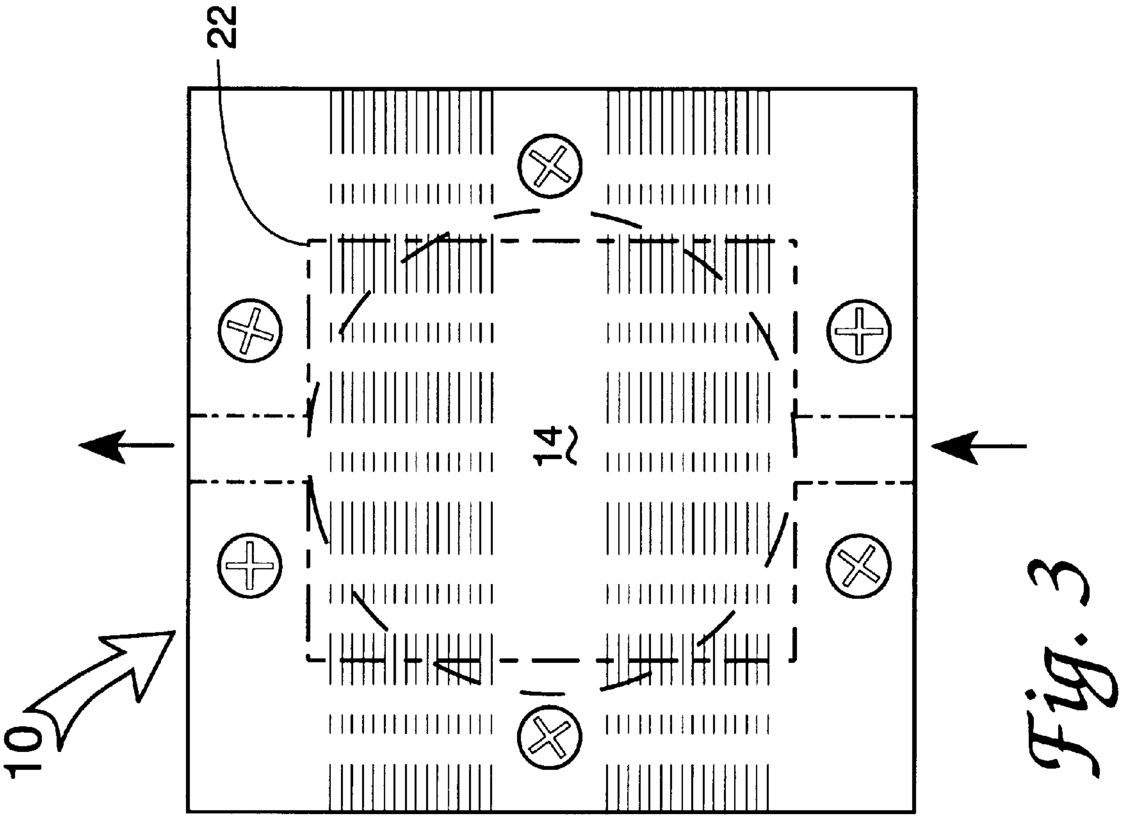
FIG. 3 is a front view of the magnetic flow cell of FIG. 1.
Figure 2:
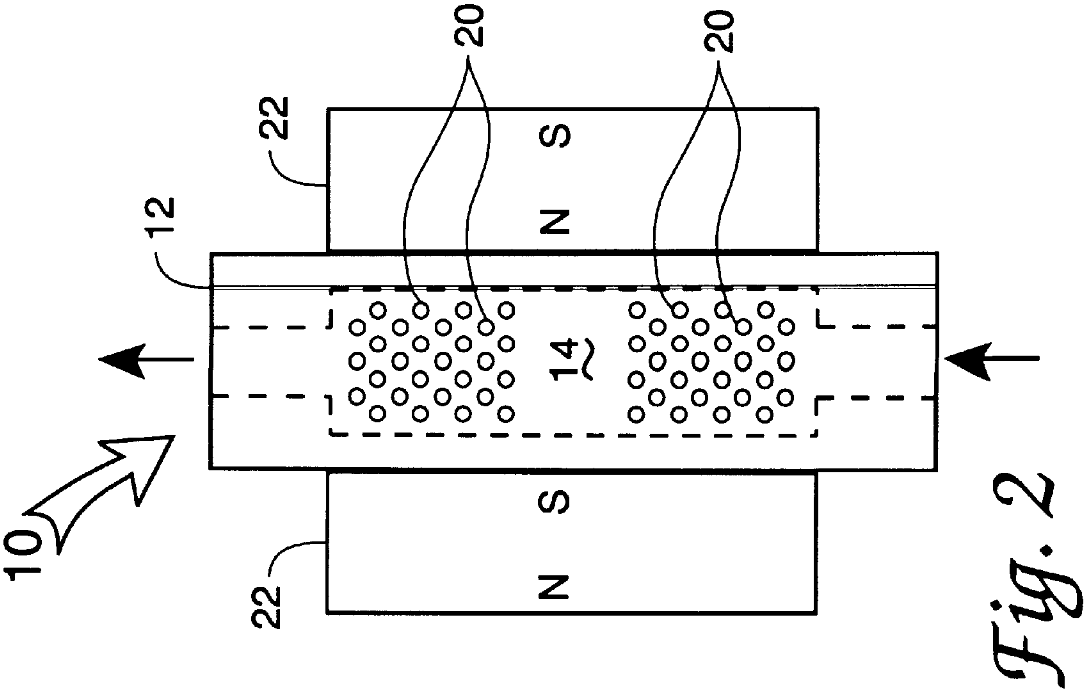
FIG. 2 is a side view of the magnetic flow cell of FIG. 1 showing the placement of a pair of flanking magnets.

Referring now to FIG. 1 of the drawings, there is shown a perspective phantom view of a magnetic flow cell, or filter block, 10 made according to the teachings of the present invention. Magnetic flow cell 10 includes a housing 12, an interior cylindrical chamber, or cavity, 14, an inlet port 16 and an outlet port 18. Two bundles of ferromagnetic rods, or pins, 20 extend across chamber 14 near inlet port 16 and outlet port 18. In a prototype of the present invention, the magnetic flow cell was 2 in. wide and made of low sample binding DELREN plastic. The ferromagnetic rods were 0.03 in. diameter stainless steel pins in two bundles of 28 rods each. A pair of 120 lb. cobalt permanent magnets 22, shown in FIG. 2 and in dashed outline in FIG. 3, flank flow cell 10 on either side when flow cell 10 is energized, and are removed from their flanking positions when flow cell 10 is de-energized. In the prototype apparatus, the cobalt magnets are each 25 mm square and 10.8 mm thick. Flanking magnets 22 in the prototype apparatus are 13 mm apart and produce a field strength of 6,600 Oe or 0.42 $W/m^2$.

Ferromagnetic rods 20 are paramagnetic, so that they are magnetic while in the presence of the magnetic field created by flanking magnets 22, and lose their magnetic state when flanking magnets 22 are removed.

The cylindrical shape of chamber 14 creates an increasing cross-sectional area that assists magnetic bead capture by retarding the flow of beads as they transit flow cell 10. While the decreasing cross-sectional area of chamber 14 tends to increase the flow rate as a fluid sample nears outlet port 18, tests have shown that the capture rate is so complete in the first half of the flow cell that this is not a problem.

The flow of a fluid sample through chamber 14 is preferably against gravity so that the flow is further retarded as the fluid sample enters the chamber, although in tests with prototypes the system has worked well with flows in either direction.

Figure 4:
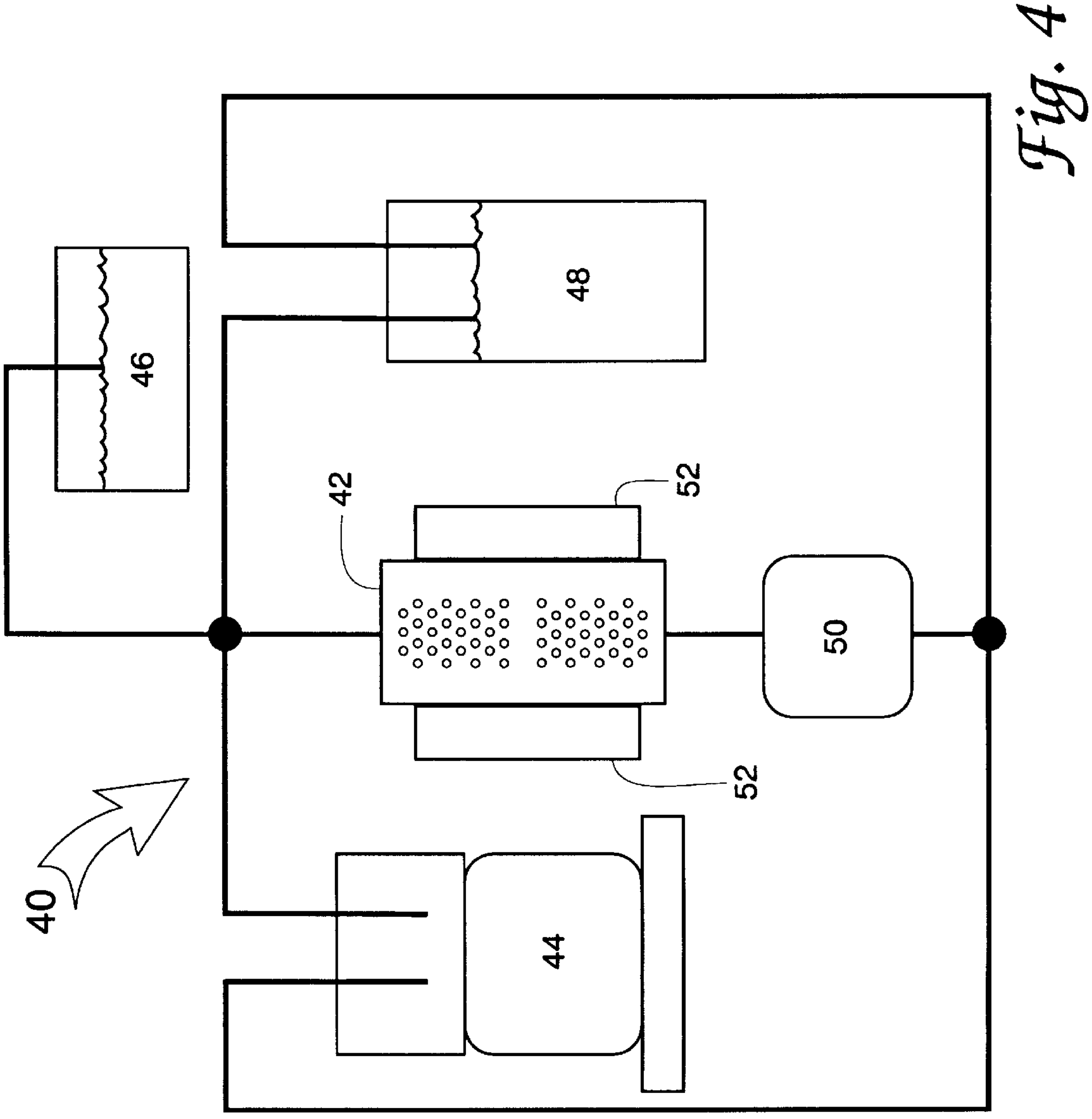
FIG. 4 is a schematic diagram of a magnetic flow cell used as part of an immunomagnetic assay system according to the teachings of the present invention.

FIG. 4 is a schematic diagram of a magnetic flow cell 42 used as part of an immunomagnetic assay system 40 according to the teachings of the present invention. Immunomagnetic assay system 40 comprises four interconnected subsystems which: (1) sequentially mix a fluid sample with antibody-magnetic beads in a reaction cycle; (2) magnetically capture the magnetic beads in a collection cycle; (3) separate non-magnetic circulating debris from the fluid sample in a rinse cycle; and finally, (4) in a filter cycle, remove the captured magnetic particles (with bound bacteria or other biological material) and capture them onto a membrane filter for a separate analysis cycle in which the material captured on the membrane filter is analyzed using, for example, fluorescence microscopy (FM), electrochemilumescence (ECL), liquid-based fluorimetric assay (FL), flow cytometry (FC), etc., which processes can be included as part of an overall computer-controlled automated process.

Immunomagnetic assay system 40 includes a magnetic flow cell 42, a sample and antibody-magnetic beads mixing chamber 44, a buffer solution reservoir 46, a rinse solution reservoir 48, a pump 50, a pair of movable magnets 52 and associated tubing and valves. All the various components and operations are computer controlled to create an automated system.

The reaction cycle starts when a dye (such as acridine orange (AO) ), a buffer solution (such as phosphate buffered saline (PBS)), antibody-coated magnetic beads and a sample (such as a bacterial sample) are brought together in mixing chamber 44 and ends when sufficient time for a reaction to occur has passed. The collection cycle then circulates the reacted fluid sample between mixing chamber 44 and magnetic flow cell 42 to isolate the target biological material (which has bonded to the antibodycoated magnetic beads) from the rest of the circulating fluid sample debris (blood cells, proteins, etc.). The collection cycle ends after the reacted fluid sample has circulated through magnetic flow cell 42 generally at least four times. Next, the rinse cycle circulates clean buffer solution between rinse solution reservoir 48 and magnetic flow cell 42. Before returning to rinse solution reservoir 48, the buffer solution passes through a 0.2 μm syringe filter (not shown) to trap potential interfering bacteria and large protein fragments. Sufficient circulating time is allowed to insure that all potential interfering bacteria and large protein fabrics have been flushed from magnetic flow cell 42 and trapped in the syringe filter. Then, in the filter cycle, magnets 52 are removed from their position flanking magnetic flow cell 42 to de-energize the flow cell and magnetic flow cell 42 is agitated, or shaken, by a mechanical vibrator (not shown) to help remove the captured magnetic beads by a reverse flow of buffer solution from buffer solution reservoir 46. The captured magnetic beads are captured on a 0.45 μm membrane filter (not shown) for the separate analysis cycle.

Pump 50 is preferably a vortex-type pump, instead of a rotor or propeller type pump, so that there is less chance for hysteresis from earlier tests from magnetic beads sticking to the rotor.

Example Sample Preparation, Invention Operation and Fluorescence Analysis

Heat killed, lyophilized *Escherichia coli O*157:H7 were obtained from Kirkegaard Perry Laboratories (KPL) in Gaithersburg, Md. Fresh adult human whole blood in citrate phosphate dextrose (seronegative for HIV, Cytomegalovirus and Hepatitis B) buffer was obtained commercially from Advanced Biotechnologies Inc. in Columbia, Md. (cat. no. 07-014-000). Biotinylated goat anti-*E. coli O*157 antibody was obtained from KPL (cat. no. 01-95-90). Rabbit anti-*E. coli* (cat. no. B65007R), chicken anti-*E. coli O*157:H7 (cat. no. B85365C) and murine monoclonal antibody to human CD8 (cat. no. P01117M) were purchased from Biodesign International in Kennebunk, Me. The anti-CD8 antibody was biotinylated by use of a Molecular Devices Corp., Menlo Park, Calif., kit. Affinity purified Texas Red-labeled rabbit-anti-chicken IgG (cat. No. 303-075-003) and Texas Red-labeled donkey-anti-rabbit IgG (cat. no. 711-075-152) were purchased from Jackson ImmunoResearch Laboratories in West Grove, Pa. Biotinylated murine monoclonal antibodies to human CD3 (cat. no. B-9905, clone UCHT-1) and CD4 (cat. no. B-7280, clone Q4120) were obtained from Sigma Chemical Co. in St. Louis, Mo., as was acridine orange (AO). Streptavidin-coated paramagnetic beads (2.8 μm diameter, M-280) beads were obtained from Dynal Corp. in Lake Success, N.Y. Streptavidin-coated colloidal ferrofluid magnetic particles, or "MACS", beads were obtained from Miltenyi Biotec Corp. in Auburn, Calif.

Various concentrations of killed *E. coli O*157:H7 were suspended in phosphate buffered saline (PBS, pH 7.4). A 20 μL volume of each suspension was assayed by an indirect sandwich technique. In these assays, 100 ng of the biotinylated KPL goat-anti-*E. coil O*157 antibody were added to 20 μg of streptavidin coated DYNAL magnetic beads for 10 min., followed by addition of 200 ng of Biodesign rabbit anti-*E. coli* or chicken anti-*E. coli O*157 antibody for 30 min. Finally, 200 ng of either appropriate type of Texas Red-conjugated reporter antibody was added for 10 min. Magnetic beads were collected using a cobalt magnet and washed in PBS, followed by resuspension in 1 ml PBS and processing by a prototype immunomagnetic assay system built according to the teachings of the present invention. All incubations were performed with gentle agitation or vortex mixing at room temperature.

Human T (CD3+) lymphocytes and T cell subsets (CD4+ and CD8+) were assayed by interrogating 1 ml samples of adult whole blood, diluted 1:10 in PBS, with 1 to 2 μg of the various biotinylated anti-CD monoclonal antibodies attached to 40 μg of streptavidin-coated magnetic beads for 1 hr. at room temperature. Leukocytes in diluted whole blood were stained with 100 μl of 0.25 μM AO for 20 min. Subsequently captured lymphocytes were washed three times in degassed PBS plus 0.1% Triton X-100 prior to processing by the prototype system.

Typical runs consisted of a 2 min. magnetic collection cycle, a 1 min. rinse cycle, and a 4 min. expulsion of captured materials by vibration of the flow cell. The fluid flow rate was maintained at 2 ml per min. Texas Red was excited at 596 nm and fluorescence intensity was measured at 620 nm, while AO was excited at 502 nm and read at 526 nm (excitation and emission maxima for AO bound to ds-DNA) by a Jasco FP-920 fluorometer. The fluorometer was operated for 4 min. during the expulsion phase, in which time fluorescence intensity peaked and returned to baseline levels. Area under these fluorescence intensity peaks was used to quantify total fluorescence after subtraction of background fluorescence levels. Controls consisting of complete assays without antigen were run to assess background fluorescence.

The prototype system was initially tested with both micron-sized (DYNAL) magnetic beads and a nm-sized colloidal ferrofluid (Miltenyi MACS beads) and worked well for both types of magnetic beads as assessed by the relatively clear color of the rinse buffer and the brown color (indicating the presence of magnetic beads, which are brown colored) of the effluent. However, magnetic flow cell retention appeared better for micron-sized magnetic beads than for the ferrofluid, which generally gave a slight tinge to the rinse buffer. While the steel pin flow cell design exhibited some hysteresis, it was relatively minor and could be eliminated by flushing with PBS between sample runs.

The potentially extreme sensitivity of this approach was illustrated by capture and detection of as little as 100 pathogenic bacteria per ml in pristine buffer. This extreme sensitivity is clearly the product of several factors. First, the rabbit anti-*E. coli* immunoassay contained relatively high affinity antibodies. By comparison the lower affinity chicken-anti-chicken antibody format gave a detection limit of only $10^4$ bacteria per ml. Second, bacterial-antibody-magnetic bead complexes were efficiently captured by the high magnetic field gradient of the present invention. Third, an indirect sandwich technique was chosen to help amplify the fluorescence signal. Finally, Texas Red was chosen as the fluorochrome, thus minimizing intrinsic background fluorescence from the bacteria and magnetic beads, which both demonstrate some green autofluorescence emission. The immunologic prozone effect was evident at high antigen concentrations, but it is clear that each bacterial assay had a "linear" dynamic range of at least three orders of magnitude in pristine buffer.

Detection of T cells was achieved in a more complex matrix (diluted blood) than buffer. Although, the CD4/CD8 ratios were lower than expected, this finding is probably more a reflection of extraneous factors, such as varying antibody affinities, than of the capability of the present invention. Antibody affinity is even more critical for immunomagnetic-assisted detection methods than for immunocytochemical or immunofluorescence staining. In the case of immunomagnetic separation, vortex mixing and instrument processing can generate relatively large shear forces that break apart target cell-antibody-magnetic bead complexes, which might otherwise be counted as positives in an immunostaining assay.

The disclosed apparatus and method for performing immunomagnetic assays successfully demonstrates a versatile immunomagnetic separator designed to efficiently capture all types of magnetic beads, including colloidal ferrofluid particles, which have minute magnetic domains and low magnetic susceptibility, in a rapid flow-through manner. Micron-sized or larger magnetic particles are easily collected by the present invention. The ability of the present invention to capture even ferrofluid particles in a flow-through manner is conferred by the magnetized flow cell pins, which act to locally "concentrate" the external magnetic field and thus increasing its effective field strength. In addition, the internal circular void design of the flow cell acts to retard the fluid flow and further assist magnetic bead capture by increasing magnetic bead residence time. Although the disclosed apparatus and method are specialized, their teachings will find application in other areas where batch processes suitable for laboratory use need to be modified for continuous use for a greater variety of samples to find utility in industrial and other larger environments.

It is understood that modifications to the invention may be made, as might occur to one with skill in the field of this invention, within the scope of the appended claim. Therefore, all embodiments contemplated have not been shown in complete detail. Other embodiments may be developed without departing from the spirit of this invention of from the scope of the appended claims.

We claim:

1. A magnetic flow cell for capturing antibody-coated magnetic beads from a fluid sample as part of an immunomagnetic assay system, comprising:

(a) a housing;

(b) a chamber inside the housing;

(c) an inlet port through the housing into the chamber for flowing the fluid sample into the chamber;

(d) an outlet port through the housing out from the chamber for flowing the fluid sample out of the chamber;

(e) a plurality of paramagnetic rods positioned inside the chamber such that the flowing fluid sample will flow past the plurality of the paramagnetic rods as it flows through the chamber, wherein the chamber is shaped so that its cross-sectional area expands from where it connects to the inlet port to a position past at least the plurality of the paramagnetic rods.

2. The magnetic flow cell according to claim 1, wherein the plurality of the paramagnetic rods are positioned perpendicularly to an axis drawn between the inlet port and the outlet port.

3. An automated immunomagnetic assay system for analysis of an analyte in a sample, comprising:

(a) a reaction subsystem for reacting magnetic beads coated with an antibody, which binds to the analyte, with the sample in a solution to make a fluid sample;

(b) a collection subsystem for capturing the magnetic beads out of the fluid sample;

(c) a rinsing subsystem for removing non-magnetic bead debris from the collection subsystem; and, (d) a filtering subsystem for removing the captured magnetic beads from the collection subsystem and holding them for the analysis.

4. The automated immunomagnetic assay system according to claim 3, wherein the collection and filtering subsystems comprise:

(a) a magnetic flow cell, the magnetic flow cell comprising (i) a housing;

(ii) a chamber inside the housing;

(iii) an inlet port through the housing into the chamber for flowing the fluid sample into the chamber;

(iv) an outlet port through the housing out of the chamber for flowing the fluid sample out of the chamber; and (v) a plurality of paramagnetic rods positioned inside the chamber perpendicular to an axis drawn between the inlet port and the outlet port such that the flowing fluid sample will flow past the plurality of the paramagnetic rods as it flows through the chamber;

(vi) wherein the chamber is shaped so that its cross-sectional area expands where it connects to the inlet port to a position past at least the plurality of the paramagnetic rods;

and, (b) a pair of movable magnets positioned such that they are movable to and from a position flanking the magnetic flow cell.

5. An automated immunomagnetic assay system for analysis of an analyte in a sample, comprising:

(a) a reaction subsystem for reacting magnetic beads coated with an antibody, which binds to the analyte, with the sample in a solution to make a fluid sample;

(b) a collection subsystem for capturing the magnetic beads out of the fluid sample;

(c) a rinsing subsystem for removing non-magnetic bead debris from the collection subsystem; and (d) a filtering subsystem for removing the captured magnetic beads from the collection subsystem and holding them for the analysis;

wherein the collection and filtering subsystems comprise:

(i) a magnetic flow cell, the magnetic flow cell comprising (1) a housing;

(2) a chamber inside the housing;

(3) an inlet port through the housing into the chamber for flowing the fluid sample into the chamber;

(4) an outlet port through the housing out of the chamber for flowing the fluid sample out of the chamber; and (5) a plurality of paramagnetic rods positioned inside the chamber such that the flowing fluid sample will flow past the plurality of the paramagnetic rods as it flows through the chamber;

wherein the chamber is shaped so that its cross-sectional area expands from where it connects to the inlet port to a position past at least the plurality of the paramagnetic rods; and, (ii) a pair of movable magnets positioned such that they are movable to and from a position flanking the magnetic flow cell.

6. The automated immunomagnetic assay system according to claim 5, wherein the plurality of the paramagnetic rods are positioned perpendicularly to an axis drawn between the inlet port and the outlet port.

7. A method for capturing antibody-coated magnetic beads from a fluid sample as part of an immunomagnetic assay system, comprising the steps of:

(a) flowing the fluid sample through a chamber, wherein the chamber comprises a plurality of paramagnetic rods positioned inside the chamber such that the flowing fluid sample flows past the plurality of the paramagnetic rods as it flows through the chamber and wherein the chamber is shaped so that its cross-sectional area expands from the fluid sample enters the chamber to a position past at least the plurality of the paramagnetic rods; and, (b) flanking the chamber with a pair of magnets as the fluid sample flows through the chamber thereby collecting the magnetic beads on the plurality of the paramagnetic rods;

(c) rinsing non-magnetic bead debris from the chamber by flowing a buffer solution through the chamber;

(d) removing the pair of magnets to release the magnetic particles from the plurality of the paramagnetic rods; and (e) capturing the released magnetic particles on a membrane filter provided in the chamber by reversing the flow of the buffer solution through the chamber.

8. The method for capturing antibody-coated magnetic beads according to claim 7, wherein the plurality of the paramagnetic rods are positioned perpendicularly to the flow of the fluid sample through the chamber.

9. A method for performing an immunomagnetic assay for an analyte in a sample, comprising the steps of:

(a) reacting magnetic beads coated with an antibody, which binds to the analyte, with the sample in a solution to make a fluid sample;

(b) collecting the magnetic beads out of the fluid sample by the steps of:

(i) flowing the fluid sample through a chamber, wherein the chamber comprises a collection subsystem comprising a plurality of paramagnetic rods positioned inside the chamber such that the flowing fluid sample flows past the plurality of the paramagnetic rods as it flows through the chamber and wherein the chamber is shaped so that its cross-sectional area expands from the fluid sample enters the chamber to a position past at least the plurality of the paramagnetic rods; and, (ii) flanking the chamber with a pair of magnets as the fluid sample flows through the chamber thereby collecting the magnetic beads on the plurality of the paramagnetic rods;

(c) rinsing non-magnetic bead debris from the collection subsystem by flowing a buffer solution through the chamber;

(d) capturing the collected magnetic beads on a membrane filter provided in the chamber by moving the pair of magnets away from the position flanking the chamber and reverse flowing the buffer solution through the chamber; and (e) analyzing the analyte bound to the magnetic beads captured on the membrane filter.

10. The method for performing an immunomagnetic assay according to claim 9, wherein the plurality of the paramagnetic rods are positioned perpendicularly to the flow of the fluid sample through the chamber.

* * * * *